United States Patent
Sasayama

(10) Patent No.: US 10,253,021 B2
(45) Date of Patent: Apr. 9, 2019

(54) METHOD FOR PRODUCING BENZOXAZOLE COMPOUND

(71) Applicant: Sumitomo Chemical Company, Limited, Tokyo (JP)

(72) Inventor: Daisuke Sasayama, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/064,481

(22) PCT Filed: Dec. 19, 2016

(86) PCT No.: PCT/JP2016/087746
§ 371 (c)(1),
(2) Date: Jun. 21, 2018

(87) PCT Pub. No.: WO2017/110729
PCT Pub. Date: Jun. 29, 2017

(65) Prior Publication Data
US 2019/0002451 A1 Jan. 3, 2019

(30) Foreign Application Priority Data
Dec. 22, 2015 (JP) .................. 2015-249417

(51) Int. Cl.
C07D 413/04 (2006.01)
(52) U.S. Cl.
CPC .................. C07D 413/04 (2013.01)
(58) Field of Classification Search
CPC ..................................... C07D 413/04
USPC ....................................... 546/271.7
See application file for complete search history.

(56) References Cited

U.S. PATENT DOCUMENTS

| | | |
|---|---|---|
| 2003/0032810 A1 | 2/2003 | Castro et al. |
| 2005/0075378 A1 | 4/2005 | Gossett et al. |
| 2015/0313234 A1 | 11/2015 | Takahashi et al. |

FOREIGN PATENT DOCUMENTS

| | | |
|---|---|---|
| EP | 0398425 A1 | 11/1990 |
| JP | H03047174 A | 2/1991 |
| JP | H07188227 A | 7/1995 |
| JP | 2002533327 A | 10/2002 |
| JP | 2005502600 A | 1/2005 |
| WO | 2014104407 A1 | 7/2014 |

OTHER PUBLICATIONS

English Translation of International Preliminary Report on Patentability dated Jun. 26, 2018 in International Application No. PCT/JP2016/087746.
English Translation of International Search Report dated Mar. 21, 2017 in International Application No. PCT/JP2016/087746.

*Primary Examiner* — Patricia L Morris
(74) *Attorney, Agent, or Firm* — Panitch Schwarze Belisario & Nadel LLP

(57) ABSTRACT

A compound represented by the formula (1)

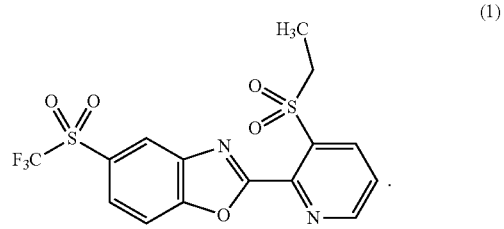

having controlling effects on harmful organisms can be produced by cyclizing a compound represented by the formula (2)

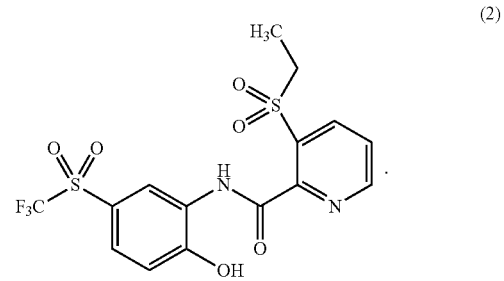

in the presence of an organic sulfonic acid and acetic anhydride in a solvent, while removing water and acetic acid to the outside of the system.

7 Claims, No Drawings

METHOD FOR PRODUCING BENZOXAZOLE COMPOUND

CROSS-REFERENCE TO RELATED APPLICATION

This application is a Section 371 of International Application No. PCT/JP2016/087746, filed Dec. 19, 2016, which was published in the Japanese language on Jun. 29, 2017, under International Publication No. WO 2017/110729 A1, which claims priority under 35 U.S.C. § 119(b) to Japanese Application No. 2015-249417, filed Dec. 22, 2015, the disclosures of which are incorporated herein by reference in their entirety.

TECHNICAL FIELD

The present invention relates to a method for producing a benzoxazole compound.

BACKGROUND ART

WO2014/104407 describes a benzoxazole compound having controlling effects on harmful organisms. Its Production Example 17 (5) describes a method for producing 2-(3-ethanesulfonylpyridin-2-yl)-5-(trifluoromethanesulfonyl)benzoxazole by cyclizing 3-ethanesulfonyl-N-[2-hydroxy-5-(trifluoromethanesulfonyl)phenyl]picolinamide under refluxing conditions in the presence of paratoluenesulfonic acid monohydrate.

SUMMARY OF THE INVENTION

The present invention provides a new method for producing 2-(3-ethane sulfonylpyridin-2-yl)-5-(trifluoromethanesulfonyl)benzoxazole, that is, a compound represented by the formula (1):

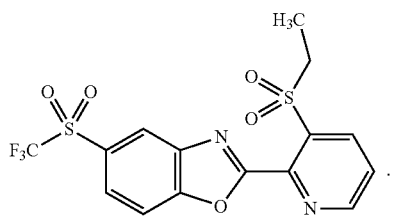

(1)

(hereinafter, described as compound (1)).

According to the present inventor, the compound (1) is produced by cyclizing a compound represented by the formula (2):

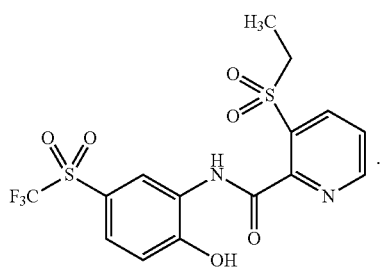

(2)

(hereinafter, described as compound (2)) in the presence of an organic sulfonic acid and acetic anhydride in a solvent, while removing water and acetic acid to the outside of the system.

EMBODIMENTS OF THE INVENTION

The present invention will be illustrated in detail below.

The compound (2) as a starting material can be produced by the method described in WO2014/104407.

In the present invention, cyclization is performed in a solvent. Examples of the solvent include aromatic hydrocarbon solvents such as toluene, xylene, ethylbenzene, cumene, and mesitylene; aromatic halogenated hydrocarbon solvents such as chlorobenzene and o-dichlorobenzene; ether solvents such as 1,4-dioxane; ester solvents such as butyl acetate; nitrile solvents such as propionitrile; sulfur-containing compound solvents such as dimethyl sulfoxide and sulfolane; amide solvents such as N,N-dimethylformamide, N,N-dimethylacetamide, and N-methylpyrrolidone, and mixed solvents thereof. Preferable examples thereof include aromatic hydrocarbon solvents and aromatic halogenated hydrocarbon solvents, and more preferable examples thereof include xylene, ethylbenzene, cumene, mesitylene, chlorobenzene, and o-dichlorobenzene.

A use amount of the solvent is usually 1 to 100 parts by mass, and preferably 1 to 20 parts by mass, based on 1 part by mass of the compound (2).

Examples of the organic sulfonic acid used in the cyclization include paratoluenesulfonic acid, benzenesulfonic acid, methanesulfonic acid, and camphorsulfonic acid. As the organic sulfonic acid, a hydrate thereof may be used, and when the hydrate is used, it is preferable that it is mixed with the solvent in advance, and the mixture is refluxed and dehydrated using a Dean-Stark apparatus or the like, and is subsequently used in the cyclization. Preferable organic sulfonic acid is paratoluenesulfonic acid, benzenesulfonic acid, and methanesulfonic acid.

For the cyclization, the organic sulfonic acid is usually used at the ratio of 0.1 mole to 5 moles, and preferably, the organic sulfonic acid is used at the ratio of 0.5 mole to 3 moles, based on 1 mole of the compound (2).

A cyclization temperature is usually in the range of 100° C. to 180° C., and preferably in the range of 130° C. to 165° C. A cyclization time is usually in the range of 0.1 to 48 hours, and preferably in the range of 0.1 to 24 hours.

For the cyclization, acetic anhydride is usually used at the ratio of 0.1 to 5 moles, and preferably, acetic anhydride is used at the ratio of 0.5 to 2 moles, based on 1 mole of the compound (2).

The cyclization is performed while acetic acid generated by a reaction of acetic anhydride and water, together with water is removed to the outside of the system.

To remove water and acetic acid to the outside of the system, water and acetic acid can be distilled off by azeotropic distillation. Since the azeotropic distillation of the solvent, water and acetic acid is preferable, it is advantageous to use xylene, chlorobenzene or mesitylene as the solvent. When the solvent is recovered and reutilized, by the azeotropic distillation of the solvent with water and acetic acid using a Dean-Stark apparatus or the like, and neutralizing acetic acid by mixing the distilled off liquid with an aqueous alkaline solution such as an aqueous sodium hydroxide solution, the solvent containing a reduced amount of acetic acid can be returned to the system. To reduce an amount of water in the system, a dehydrating agent such as molecular sieves, anhydrous sodium sulfate or anhydrous magnesium sulfate can be added to the system before the cyclization. These dehydrating agents can be removed by filtration after completion of the cyclization.

After completion of the cyclization, the reaction mixture is added to water, or alkaline water such as an aqueous potassium carbonate solution, the mixture is extracted with an organic solvent, and the organic layer is concentrated; the reaction mixture is added to water, and the generated solid is collected by filtration; or the solid generated in the reaction mixture is collected by filtration, thereby, the compound (1) can be isolated. The isolated compound (1) can also be further purified by recrystallization, chromatography or the like.

EXAMPLES

The present invention will be illustrated below by way of examples, but the present invention is not limited to these examples.

Example 1

Under the nitrogen atmosphere, a mixture of 29.6 g of paratoluenesulfonic acid monohydrate and 30.2 g of xylene was refluxed and dehydrated for 4 hours using a Dean-Stark apparatus. To a mixture of 50.0 g of a compound (2) and 60 g of xylene was added the previously obtained mixture of paratoluenesulfonic acid and xylene. Using a Dean-Stark apparatus, a straight-tube part of which had been filled with 9.5 g of a 48% aqueous sodium hydroxide solution in advance, the resulting mixture was heated to 140° C., and 5.82 g of acetic anhydride was added dropwise over 17 hours, while removing water and acetic acid to the outside of the system. The mixture was stirred at 140° C. for 7 hours, while using the Dean-Stark apparatus. The resulting mixture was added to an aqueous potassium carbonate solution, the two liquid layers were separated, a part of the resulting organic layer was quantitated using high performance liquid chromatography, and it was found that the compound (1) was obtained at a yield of 93.5%.

After the organic layer was washed with an aqueous potassium carbonate solution and water, it was concentrated and crystallized using heptane, thereby, the compound (1) was obtained at a yield of 90.2%.

Example 2

Under the nitrogen atmosphere, a mixture of 29.5 g of paratoluenesulfonic acid monohydrate and 30.1 g of xylene was refluxed and dehydrated for 4 hours using a Dean-Stark apparatus. To a mixture of 50.0 g of a compound (2) and 60 g of xylene was added the previously obtained mixture of paratoluenesulfonic acid and xylene. Using a Dean-Stark apparatus, a straight-tube part of which had been filled with 11.4 g of a 48% aqueous sodium hydroxide solution in advance, the resulting mixture was heated to 140° C., and 6.99 g of acetic anhydride was added dropwise over 18 hours, while removing water and acetic acid to the outside of the system. The mixture was stirred at 140° C. for 1 hour, while using the Dean-Stark apparatus. The resulting mixture was added to an aqueous potassium carbonate solution, the two liquid layers were separated, a part of the resulting organic layer was quantitated using high performance liquid chromatography, and it was found that the compound (1) was obtained at a yield of 93.9%.

Example 3

Under the nitrogen atmosphere, a mixture of 35.4 g of paratoluenesulfonic acid monohydrate and 36.0 g of chlorobenzene was refluxed and dehydrated for 4 hours using a Dean-Stark apparatus. To a mixture of 60.0 g of a compound (2) and 72.0 g of chlorobenzene was added the previously obtained mixture of paratoluenesulfonic acid and chlorobenzene. Using a Dean-Stark apparatus, a straight-tube part of which had been filled with 12.4 g of a 48% aqueous sodium hydroxide solution and 19.9 g of water in advance, the resulting mixture was heated to 133° C., and 11.18 g of acetic anhydride was added dropwise over 17 hours, while removing water and acetic acid to the outside of the system. The resulting mixture was added to an aqueous potassium carbonate solution, the two liquid layers were separated, a part of the resulting organic layer was quantitated using high performance liquid chromatography, and it was found that the compound (1) was obtained at a yield of 95.4%.

Example 4

Under the nitrogen atmosphere, a mixture of 38.2 g of paratoluenesulfonic acid monohydrate and 38.4 g of mesitylene was refluxed and dehydrated for 2 hours and 40 minutes using a Dean-Stark apparatus. To a mixture of 83.7 g of a compound (2) and 201 g of mesitylene was added the previously obtained mixture of paratoluenesulfonic acid and mesitylene. The resulting mixture was heated to 165° C., and 16.77 g of acetic anhydride was added dropwise over 11 hours, while distilling off water, acetic acid, and mesitylene. An amount of the distilled off liquid at that time was 146 g, and that of mesitylene added dropwise was 147 g. The reaction rate of the resulting mixture was determined using high performance liquid chromatography, and found to be 99%.

Reference Example 1

Under the nitrogen atmosphere, a mixture of 10.0 g of a compound (2) and 20.0 g of xylene was heated to 140° C. While the resulting mixture was heated at 140° C., and water and acetic acid were removed to the outside of the system using a Dean-Stark apparatus with 5.9 g of a 18.5% aqueous sodium hydroxide solution added thereto, a mixed solution of 1.40 g of acetic anhydride and 5.0 g of xylene was added dropwise over 17 hours. The resulting mixture was diluted by adding acetonitrile thereto, a part of the mixture was quantitated using high performance liquid chromatography, and it was found that a compound (1) was obtained at a yield of 6.4%.

INDUSTRIAL APPLICABILITY

According to the present invention, the compound (1) having controlling effects on harmful organisms can be produced.

The invention claimed is:

1. A method for producing a compound represented by the formula (1):

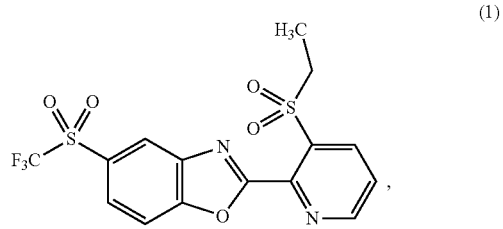 [SMILES: CCS(=O)(=O)c1cccnc1-c1nc2cc(S(=O)(=O)C(F)(F)F)ccc2o1]

the method comprising cyclizing a compound represented by the formula (2):

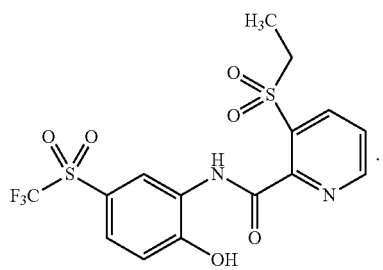

in the presence of an organic sulfonic acid and acetic anhydride in a solvent, while removing water and acetic acid to the outside of the system.

2. The method according to claim 1, wherein the solvent is one or more solvents selected from the group consisting of an aromatic hydrocarbon solvent and an aromatic halogenated hydrocarbon solvent.

3. The method according to claim 1, wherein the solvent is xylene.

4. The method according to claim 1, wherein the solvent is chlorobenzene.

5. The method according to claim 1, wherein the solvent is mesitylene.

6. The method according to claim 1, wherein the organic sulfonic acid is paratoluenesulfonic acid, methanesulfonic acid or benzenesulfonic acid.

7. The method according to claim 1, wherein the organic sulfonic acid is paratoluenesulfonic acid.

* * * * *